US012565460B2

(12) United States Patent (10) Patent No.: US 12,565,460 B2
Zellhuber et al. (45) Date of Patent: Mar. 3, 2026

(54) PROCESS AND SYSTEM FOR PREPARING A TARGET COMPOUND

(71) Applicants: LINDE GMBH, Pullach (DE); Clariant International Ltd., Muttenz (CH)

(72) Inventors: Mathieu Zellhuber, Martinsried (DE); Martin Schubert, Munich (DE); Andreas Meiswinkel, Rimsting (DE); Wolfgang Muller, Munich (DE); Gerhard Mestl, Bruckmühl (DE); Klaus Wanninger, Bruckmühl (DE); Peter Scheck, Munich (DE)

(73) Assignees: Linde GmbH, Pullach (DE); Clariant International Ltd., Muttenz (CH)

( * ) Notice: Subject to any disclaimer, the term of this patent is extended or adjusted under 35 U.S.C. 154(b) by 0 days.

(21) Appl. No.: 18/549,581

(22) PCT Filed: Mar. 14, 2022

(86) PCT No.: PCT/EP2022/056568
§ 371 (c)(1),
(2) Date: Sep. 7, 2023

(87) PCT Pub. No.: WO2022/194792
PCT Pub. Date: Sep. 22, 2022

(65) Prior Publication Data
US 2024/0294447 A1 Sep. 5, 2024

(30) Foreign Application Priority Data
Mar. 15, 2021 (DE) ......................... 102021202492.0

(51) Int. Cl.
*C07C 6/04* (2006.01)
*B01J 19/24* (2006.01)
*C07C 5/333* (2006.01)

(52) U.S. Cl.
CPC ......... *C07C 5/3332* (2013.01); *B01J 19/2425* (2013.01); *C07C 5/3335* (2013.01);
(Continued)

(58) Field of Classification Search
CPC . B01J 8/04; C07C 5/48; C07C 51/215; C07C 11/04; C07C 53/08; C07C 6/04
See application file for complete search history.

(56) References Cited

U.S. PATENT DOCUMENTS 8,519,210 B2 8/2013 Arnold et al.
11,014,075 B2 5/2021 Mestl et al.
(Continued)

FOREIGN PATENT DOCUMENTS

DE 19837519 A1 2/2000
DE 102017000848 A1 8/2018
(Continued)

OTHER PUBLICATIONS

International Search Report and Written Opinion issued in related App. No. PCT/EP2022/056568, mailed Jul. 27, 2022.
(Continued)

*Primary Examiner* — Sharon Pregler
(74) *Attorney, Agent, or Firm* — Avek IP, LLC

(57) ABSTRACT

A method for producing a target compound includes distributing a feed mixture containing ethane to multiple reaction tubes of a shell-and-tube reactor arranged in parallel, and subjecting to an oxidative catalytic conversion of the ethane in the reaction tubes. The catalytic reaction is carried out by means of catalysis zones with different activity arranged in series in the reaction tubes. One or more catalytically active materials and one or more catalytically inactive materials are provided in each of the catalysis zones. The different activity of the catalysis zones is effected by providing the one or more catalytically active materials
(Continued)

having identical or essentially identical basic formulation, wherein the one or more catalytically active materials is or are prepared using different calcination intensities.

20 Claims, 4 Drawing Sheets

(52) U.S. Cl.
CPC ................. *B01J 2219/00054* (2013.01); *B01J 2219/00162* (2013.01); *C07C 2523/22* (2013.01); *C07C 2523/28* (2013.01); *C07C 2527/057* (2013.01)

(56) References Cited

U.S. PATENT DOCUMENTS

| | | | | |
|---|---|---|---|---|
| 11,401,220 | B2 * | 8/2022 | Bos ............................ | B01J 8/04 |
| 12,012,377 | B2 * | 6/2024 | Zellhuber ................. | C07C 5/48 |
| 2010/0256432 | A1 | 10/2010 | Arnold et al. | |
| 2018/0170838 | A1 | 6/2018 | Cao et al. | |
| 2019/0055177 | A1 | 2/2019 | Bos et al. | |
| 2024/0150261 | A1 | 5/2024 | Zellhuber et al. | |
| 2024/0150263 | A1 | 5/2024 | Zellhuber et al. | |
| 2024/0158322 | A1 | 5/2024 | Zellhuber et al. | |
| 2024/0294447 | A1 | 9/2024 | Zellhuber et al. | |

FOREIGN PATENT DOCUMENTS

| | | | |
|---|---|---|---|
| DE | 102017000861 | A1 | 8/2018 |
| EP | 1164120 | A2 | 12/2001 |
| EP | 2716621 | A1 | 4/2014 |
| EP | 2716622 | A1 | 4/2014 |
| EP | 3339277 | A1 | 6/2018 |
| EP | 3476471 | A1 | 5/2019 |
| EP | 3558910 | B1 | 12/2020 |
| RU | 2214383 | C1 | 10/2003 |
| RU | 2335485 | C2 | 10/2008 |
| RU | 2730518 | C2 | 8/2020 |
| WO | 2010115099 | A1 | 10/2010 |
| WO | 2013021034 | A1 | 2/2013 |
| WO | 2013164418 | A1 | 11/2013 |
| WO | 2017144584 | A1 | 8/2017 |
| WO | 2018082945 | A1 | 5/2018 |
| WO | 2018115416 | A1 | 6/2018 |
| WO | 2018115418 | A1 | 6/2018 |
| WO | 2018141652 | A1 | 8/2018 |
| WO | 2018141653 | A1 | 8/2018 |
| WO | 2019243480 | A1 | 12/2019 |
| WO | 2020072163 | A1 | 4/2020 |
| WO | 2020074750 | A1 | 4/2020 |

OTHER PUBLICATIONS

Substantive examination report with English description issued Oct. 20, 2025 in Saudi Arabia Application No. 523450721, 10 pages.

* cited by examiner

PROCESS AND SYSTEM FOR PREPARING A TARGET COMPOUND

CROSS-REFERENCE TO RELATED APPLICATIONS

This application is the national phase of, and claims priority to, International Application No. PCT/EP2022/056568, filed Mar. 14, 2022, which claims priority to German Patent Application No. DE102021202492.0, filed Mar. 15, 2021.

FIELD OF THE INVENTION

The invention relates to a method and apparatus for producing a target compound.

BACKGROUND

The oxidative dehydrogenation (ODH) of kerosenes with two to four carbon atoms is known in principle. In ODH, said kerosenes are reacted with oxygen to form, among other things, the respective olefins and water. The invention relates to the oxidative dehydrogenation of ethane to ethylene, hereinafter also referred to as ODHE.

ODH(E) can be advantageous over more established olefin production processes such as steam cracking or catalytic dehydrogenation. For example, there is no thermodynamic equilibrium limitation due to the exothermic nature of the reactions involved and the virtually irreversible formation of water. ODH(E) can be carried out at comparatively low reaction temperatures. In principle, no regeneration of the catalysts used is required, since the presence of oxygen enables or causes in situ regeneration. Finally, in contrast to steam cracking, smaller amounts of worthless by-products such as coke are formed.

For further details regarding ODH(E), reference should be made to relevant literature, for example, Ivars, F. and López Nieto, J. M., Light Alkanes Oxidation: Targets Reached and Current Challenges, in Duprez, D. and Cavani, F. (eds.), Handbook of Advanced Methods and Processes in Oxidation Catalysis: From Laboratory to Industry, London 2014: Imperial College Press, pages 767-834, or Gärtner, C. A. et al, Oxidative Dehydrogenation of Ethane: Common Principles and Mechanistic Aspects, ChemCatChem, vol. 5, no. 11, 2013, pages 3196 to 3217, and X. Li, E. Iglesia, Kinetics and Mechanism of Ethane Oxidation to Acetic Acid on Catalysts Based on Mo—V—Nb Oxides, J. Phys. Chem. C, 2008, 112, 15001-15008, referenced.

In particular, MoVNb-based catalyst systems have shown promise for ODH(E), as mentioned, for example, in F. Cavani et al, "Oxidative dehydrogenation of ethane and propane: How far from commercial implementation?", Catal. Today, 2007, 127, 113-131, mentioned. Additional Te-containing catalyst systems can also be used. Where reference is made herein to a "MoVNb-based catalyst system" or a "MoVTeNb-based catalyst system", this is to be understood to mean a catalyst system comprising the elements mentioned as a mixed oxide, also expressed respectively as $MoVNbO_x$ and $MoVTeNbO_x$. The indication of Te in brackets stands for its optional presence. The invention is used in particular with such catalyst systems.

In the case of ODH, significant amounts of the respective carboxylic acids of the kerosenes used, in particular acetic acid in the case of ODHE, are formed as by-products under industrially relevant reaction conditions, especially when $MoVNb(Te)O_x$-based catalysts are used. For economical plant operation, a co-production of olefins and the carboxylic acids is therefore generally unavoidable when using the catalyst type described, although a preferential formation of olefins is desirable.

According to the state of the art, ODH(E) is preferably carried out in fixed-bed reactors, in particular in cooled shell-and-tube reactors, for example with molten salt cooling. For strongly exothermic reactions, i.e. in particular oxidative reactions, which also includes ODH(E), the use of a reactor bed with several zones is generally known. Basic principles are described, for example, in WO 2019/243480 A1 of the applicant. This document discloses the principle that different catalyst beds or corresponding reaction zones, which have different catalyst loadings and/or catalyst activities per unit space, are used.

In particular, the aforementioned measures serve to enable temperature and selectivity control in an ODH(E) reactor for practical technical implementation. The invention sets itself the task of improving corresponding measures.

SUMMARY

According to one embodiment of the invention, a method for producing a target compound includes distributing an ethane-containing feed mixture to multiple parallel reaction tubes of a shell-and-tube reactor and subjecting the ethane-containing feed mixture to an oxidative catalytic reaction of the ethane in the reaction tubes. The catalytic reaction is carried out by means of catalysis zones having different activities and arranged in series in the reaction tubes. One or more catalytically active materials and one or more catalytically inactive materials are provided in the catalysis zones. The different activity of the catalysis zones is effected by providing the one or more catalytically active materials with identical or essentially identical basic formulation, the one or more catalytically active materials being prepared using different calcination intensities.

According to another embodiment of the invention, a plant for producing a target compound includes a shell-and-tube reactor having multiple reaction tubes arranged in parallel and means adapted to distribute a feed mixture containing ethane to the reaction tubes and to subject it to an oxidative catalytic reaction in the reaction tubes. Catalysis zones having different activities and arranged in series are provided for the catalytic reaction in the reaction tubes. One or more catalytically active materials and one or more catalytically inactive materials are provided in the catalysis zones. The different activity of the catalysis zones is effected by providing the one or more catalytically active materials with identical or essentially identical basic formulation, wherein the one or more catalytically active materials is or are prepared using different calcination intensities.

WRITTEN DESCRIPTION

As mentioned, WO 2019/243480 A1 discloses the use of catalyst beds or corresponding reaction zones with different catalyst loadings and/or catalyst activities per unit space, using layers with variable catalyst activity provided by changing the proportion of inert material, for example, in the catalyst particles. However, the formulation of the active catalyst material itself is kept the same for all catalyst beds or reaction zones. In particular, this formulation comprises all steps of the production process, i.e. also includes steps such as drying and calcination, which are thus carried out in a uniform manner and under the same conditions. In this way, a catalytically active material with identical properties is obtained, which is diluted by the use of catalytically inactive material (binder, carrier . . . ) in order to obtain an adjustment of the catalyst activity.

Figure 4:
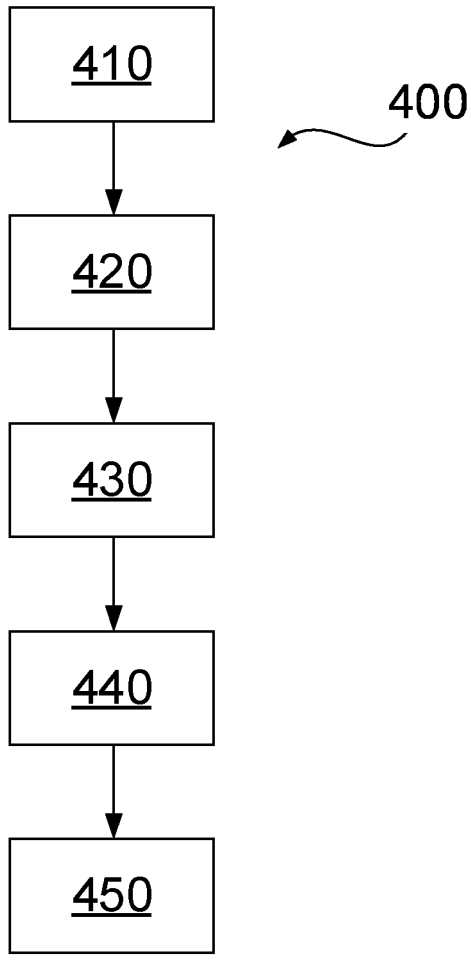
FIG. 4 illustrates the production of a catalytically active material according to one embodiment of the invention in simplified schematic form.

With respect to the terms "basic formulation" and "formulation", reference is also made to the explanation of FIG. 4. A preparation of an active catalyst material for use in the invention comprises one or more first preparation steps, a calcination following these first preparation steps, and one or more second preparation steps following the calcination. In this context, the basic formulation comprises the first manufacturing steps in an identical or essentially identical form, but not necessarily a calcination carried out identically or essentially identically. In contrast, the term formulation is intended to denote identically or essentially identically performed first manufacturing steps as well as identically or essentially identically performed calcination. In the terminology used herein, materials with an identical basic formulation or formulation are produced from identical or essentially identical starting materials. Materials with an identical basic formulation or formulation are characterized in particular by an identical element composition.

For example, for an "identical basic formulation", starting components, in particular metals, can be provided in the same form, i.e. in particular in the form of the same soluble metal salts or in the form of the same metal oxides, and these can be used in essentially the same quantities or proportions—apart from any variations which are unavoidable, for example, for manufacturing reasons or which are insignificant with regard to the catalyst properties. Furthermore, the production process here, for example by a hydrothermal synthesis, is identical or essentially identical except in particular for the calcination conditions or other parameters influencing the activity, such as the temperature or duration of certain production steps.

The term "essentially identical" is understood here to mean in particular an identity that lies within the technical tolerance limits of a corresponding process, or that a certain effect or result can be achieved within a certain tolerance by several process steps carried out "essentially identically". Such a result may in particular be a conversion-selectivity behavior.

In this context, "conversion-selectivity behavior" refers to a relationship between the conversion of a starting compound, in this case ethane, and a selectivity to the target compound, in this case ethylene, both expressed as a percentage. The conversion refers to the proportion of the starting compound that is converted to any other compound, and the selectivity refers to the proportion of the target compounds to all such compounds. An "essentially identical" conversion-selectivity behavior is thereby present in the terminology used here if the—with essentially identical conversions of the one starting compound, in particular conversions of the ethane—essentially identical selectivities to the respective target compounds are obtained. Essentially equal conversions are present if the conversions of the different catalytically active materials differ relative to one another by no more than 2 percentage points, preferably by no more than 1.5 percentage points, particularly preferably by no more than 1 percentage point, or by no more than 6%, preferably by no more than 4%, particularly preferably by no more than 2.5%. Essentially equal selectivities to a target compound are present if the selectivities to the one target compound of the different catalytically active materials, with essentially equal conversions, do not differ relative to one another by more than 1 percentage point, preferably by no more than 0.7 percentage point, particularly preferably by no more than 0.5 percentage point, or by no more than 7%, preferably by no more than 5% and particularly preferable by no more than 3%.

In the terminology used here, "calcination" means in particular heating a corresponding material to temperatures of at least 400° C. ("calcination temperature") in an atmosphere essentially containing nitrogen or pure nitrogen for a predetermined duration ("calcination time"). The calcination duration and calcination temperature define in particular the calcination intensity, whereby, if necessary, a lower calcination temperature can be cancelled or compensated by a higher calcination duration, and vice versa. In particular in the context of the embodiments described below, calcination is also referred to synonymously as "activation".

In the following, for reasons of clarity, a distinction is always made between a "catalytically active material", the actual catalyst, and a "catalytically inactive material", which itself does not have a catalytic effect but is provided together with the catalyst. The catalytically inactive material can be, for example, silica ($SiO_2$), aluminium oxide ($Al_{23}$), silicon carbide (SiC) or graphite. In particular, silicon carbide and graphite are very advantageous inert materials for (strongly) exothermic reactions such as the oxidation of alkanes, especially ODHE, since, in addition to the effect of dilution, they are particularly good thermal conductors and thus also contribute to effective thermal management of the reaction. For shaping (tabletting) the catalysts, wax is also required, but this is burned out after shaping is complete. The wax is thus no longer present in the actual catalyst, but instead leaves behind corresponding pores that are important for the accessibility of the reactants to the catalytically active centers. Above-mentioned inert materials can be used for tabletting or as framework materials for suitable catalyst shaped bodies of any kind, or they can be further bodies not equipped with catalytically active material. A catalytically inactive material is also referred to hereinafter as an "inert material".

As explained below, the catalyst beds or reaction zones produced according to embodiments of the invention offer advantages over such a prior art method, which include in particular an improved service life or durability of the catalyst, since it has a more homogeneous activity distribution. In addition, a further unexpected advantage results from the initially supposedly disadvantageous lower activity of catalytic zones provided according to embodiments of the invention.

If different activity gradations are achieved in the manner known from the prior art, i.e. by (i) dilution by physical mixing of active full catalyst shaped bodies and inert shaped bodies within a layer, or (ii) by catalyst shaped bodies which already contain the diluting inert portion in the shaped body itself, a decisive disadvantage can result from this: such layers (i) or layers of such diluted shaped bodies (ii) always consist, on the one hand, of more or less large areas which are either inert and thus inactive for the reaction, and, on the other hand, of areas which exhibit maximum (full) catalytic activity. The catalytic activity is therefore not homogeneously distributed. The reaction therefore takes place exclusively in these fully active areas. Thus, these areas are subject to very high local thermal stress with local temperature hotspots. On the one hand, this leads to faster aging of the catalyst (comprising the catalytically active material and the catalytically inactive material), for example, due to sintering or, in extreme cases, loss of mechanical stability of a catalyst shaped body due to the (very local) thermal stress. On the other hand, the selectivity is negatively affected, i.e. in particular the total oxidation of the reactant used, such as an alkane, especially ethane, is favored at too high a temperature. These effects are amplified the larger the areas of such inhomogeneities are with respect to the distribution of the catalyst activity (dilution with inert particles versus dilution within a catalyst particle).

Even if the measures proposed in the prior art initially make it possible to implement a simple and apparently relatively inexpensive production method that uses the same formulation (i.e. with identical or essentially identical calcination conditions), the disadvantages mentioned above and those mentioned below remain:

1. At the active particle, there is nevertheless a very high activity and thus local loading and temperature increase. This leads to corresponding selectivity losses and possibly also accelerated catalyst aging.
2. The insertion of inert material is often limited, for example by difficulties in shaping, stability and durability of the final catalyst shaped bodies.
3. Although the inert material is not catalytically active, it can also have a pore structure, which is then also subject to aging. The changing internal diffusion may have different aging kinetics than the chemical aging of the catalytically active material, making uniform predictable aging difficult. This can significantly complicate the calculation of service life and the predetermination of the end of life of the catalyst bed. However, such predetermination is necessary in practice in order to be able to plan maintenance intervals with catalyst replacement in a large commercial plant in good time.
4. In addition, the catalytically inactive material occupies available reactor volume that could be filled with catalytically active material. Thus, with such a solution, one typically always loses reaction space and thus space-time productivity.
5. Due to the aforementioned different aging characteristics, aging of the inert material in particular can also occur, making a catalyst change necessary, although the actual catalytically active material is still sufficiently active and selective.

The invention minimizes or avoids the use of inert material to dilute the active catalyst mass, i.e. the catalytically active material with catalytically inactive material, but typically using a certain (but especially constant) amount of catalytically inactive material (to form shaped bodies, i.e. tabletting). Within the scope of the invention, it is proposed to carry out a production of tailor-made catalysts with a specifically adjusted conversion-selectivity behavior and a specifically adjusted activity per volume, which can be used in a particularly efficient process, especially for olefin production by means of oxidative dehydrogenation of ethane.

Overall, within the scope of the invention, a method is proposed for the preparation of a target compound, in which a feed mixture containing ethane is distributed to multiple parallel reaction tubes of a shell-and-tube reactor and is subjected to an oxidative catalytic conversion of the ethane in the reaction tubes, wherein the catalytic conversion is carried out by means of catalysis zones having different activities arranged in series in the reaction tubes, and wherein one or more catalytically active materials and one or more catalytically inactive materials are provided in each of the catalysis zones. According to the invention, the different activity of the catalysis zones is brought about by providing the one or more catalytically active materials with identical basic formulation and, in particular, identical elemental composition. In particular, the activity can increase from zone to zone, i.e. in a subsequent zone in particular by more than 10%, 20% or 25% higher than in the respective preceding zone. A proportion of the one or more, catalytically inactive materials in the respective catalysis zones to a total filling of the respective catalysis zones thereby differs in particular by no more than 25%, 20%, 15%, 10% or 5% between the catalysis zones. Thus, in embodiments of the invention, the adjustment of the catalytic activity takes place exclusively or primarily due to the activity influence, in particular due to the different calcination conditions and in particular due to the different calcination intensity.

In other words, in deviation from the prior art, the invention neither (exclusively) envisages the use of elementally differently composed catalyst materials nor (exclusively) the use of differently diluted catalyst materials. This leads to the advantages already described in detail above.

The one or at least one of the multiple catalytically active materials comprises at least the metals molybdenum, vanadium, niobium and optionally tellurium. The one or at least one of the multiple catalytically active materials is/are further made in particular at least in part from the oxides of said metals. This catalytically active material can thus be produced from precursors that are commercially available in large quantities and at low prices. The disadvantages of production from (water) soluble precursors of the metals, such as ammonium heptamolybdate or vanadyl sulfate, can thus be avoided. Telluric oxide can be used instead of telluric acid. In particular, the catalytically active material can be prepared (completely) using the oxides $MoO_3$, $V_2O_5$, $Nb_2O_5$ and $TeO_2$.

As explained below with reference to specific embodiments of the invention, a catalytically active material prepared on the basis of the metal oxides (as described, for example, in Example 1 of DE 10 2017 000 861 A1) may have a lower activity than a catalytically active material prepared on the basis of the soluble precursors. However, in the conversion of ethane with comparable overall selectivity to the commercial value products ethylene and acetic acid, a higher selectivity to ethylene can be observed for a catalytically active material of the corresponding type prepared on the basis of the metal oxides. The same can be expected for the conversion of other alkanes.

Without being bound by theory, this fact, as explained in connection with the embodiment examples, may result in a flatter temperature profile detectable when using an appropriate catalytically active material. By this effect, a reduction of the risk of thermal runaway of the catalyst bed or a part of the catalyst bed or a reaction zone in a reactor can be achieved. A higher catalyst bed inlet temperature can be used to achieve the same conversion.

Surprisingly, therefore, the supposed disadvantage of a lower activity, in particular of a catalyst prepared via the pure oxides, turns out to be particularly advantageous in the sense of the invention, since the reduced activity means that the process can or should be operated at somewhat higher temperatures. This in turn then results in an increased yield of the particularly preferred value product ethylene.

In the method proposed according to the invention, the one or the at least one of the several, catalytically active materials is produced in particular using a hydrothermal synthesis, as is also already known in principle from the aforementioned DE 10 2017 000 861 A1.

A different activity of the one or at least one of the multiple, catalytically active materials in the reaction zones is, in contrast to WO 2019/243480 A1, brought about in the context of the invention by different calcination intensities. In other words, the one or are the multiple catalytically active materials in the different reaction zones is produced using the identical basic formulation but different calcination intensities. Therefore, as exploited according to the invention, these exhibit different activities even without different inert fractions.

The basic formulation decisively influences the conversion-selectivity behavior of a corresponding catalytically active material. The activity of the catalytically active material can thereby be adapted for a specific basic formulation, as recognized according to the invention, by selecting suitable calcination conditions. In particular, the calcination conditions thereby comprise the selection of the calcination process technology, i.e. continuous or discontinuous calcination, and the selection of the calcination intensity (the calcination intensity is defined in particular by a calcination temperature and/or a calcination time). Further details are also explained below with reference to a specific embodiment. As recognized according to the invention and evidenced by the embodiments, in particular, the calcination intensity (temperature and duration) alone is a suitable parameter to cause the differential activity of the one or at least one of the multiple catalytically active materials. Other parameters may, but do not need to be altered.

In other words, in one embodiment, the invention takes advantage of the fact that the activity of a particular catalyst material, and relatedly also other parameters such as the start-up temperature, can be influenced by the preparation and in particular by a single preparation step. It was found, in particular for the $MoVNb(Te)O_x$ catalysts advantageously used according to the invention, that the calcination conditions and in particular the calcination intensity have a direct influence on their respective activity. Increased activity is accompanied by a reduced start-up temperature. The catalytically active material itself remains basically the same in terms of composition and can in particular be taken from the same synthesis approach and (apart from calcination) the same synthesis and production processes, which corresponds to the basic formulation defined above.

Within the scope of the invention, it was surprisingly found that the physicochemical properties, in particular in the form of the BET surface area and/or the specific pore volume, of catalyst materials prepared with the identical basic formulation can be influenced by the choice of calcination conditions and in particular by the choice of calcination intensity. Thereby, a higher calcination intensity leads to a reduction of the BET surface area and, more significantly, to a reduction of the specific pore volume. Furthermore, surprisingly, for the catalyst materials prepared in this way (i.e. identical basic formulation, different calcination intensity), the correlation was found between the BET surface area and, more significantly, between the specific pore volume and the catalytic activity, namely that the catalytic activity increases with increasing specific pore volume (or higher BET surface area). Thus, the specific pore volume or BET surface area is suitable as a guide parameter for the preparation of the catalyst materials.

As just explained, a higher activity is usually accompanied by a higher pore volume and/or a higher BET surface area. As clarified in the embodiment examples, this refers to the pore volume or BET surface area of the catalyst material before shaping, i.e. after calcination. The BET surface area represents the mass-based specific surface area, which is calculated from experimental data according to known procedures and is usually expressed in units of square meters per gram ($m^2 \cdot g^{-1}$). The BET measurement is known to the skilled person from relevant textbooks and standard works, for example DIN ISO 9277:2003-05, "Determination of the specific surface area of solids by gas adsorption using the BET method (ISO 9277:1995)". However, this is not a necessary mandatory requirement for the implementation of the invention, but concerns a possible embodiment. The specific pore volume of a catalyst can be determined, for example, with the aid of nitrogen physisorption measurements, i.e. basically with the same measurement method that is also used to determine the BET surface area, using the part of the sorption isotherm at relative pressures of about 1 $p/p_0$ to determine the specific pore volume.

In a corresponding embodiment, a pore volume and/or a BET surface area thus differ in at least two of the catalysis zones, whereby in particular deviations of 15 to 60% can occur, i.e. the pore volume or BET surface area of the catalyst material of the first catalysis zone can be 15 to 60% smaller than the pore volume or BET surface area of the second catalysis zone (as explained above, the pore volume or BET surface area refers to the catalyst material after calcination before shaping). As just explained, the pore volume can be used in particular as a measure of catalyst activity.

One advantage is that the one or at least one of the multiple catalytically active materials in one of the catalysis zones may have an activity that is more than 10% higher than the one or at least one of the multiple catalytically active materials in another of the catalysis zones due to a different calcination intensity. The activity may also be, for example, 20%, 30% or 40% higher.

In the method proposed according to the invention, one advantage is that at least two different layers of catalyst are used, each with (essentially) the same proportion of binder or carrier (i.e. catalytically inactive material), but with different activity of the catalytically active material. In other words, one advantage is that a proportion of the one or more catalytically inactive materials in the different catalysis zones differs relative to one another by no more than 25%, 15%, 10% or 5%, and in particular only within the scope of dosing or production tolerances.

As mentioned above, the invention is used in connection with an ODH of ethane (ODHE), such that the feed mixture contains oxygen and, as a kerosene, ethane, and the oxidative conversion is carried out as an oxidative dehydrogenation of ethane. Therefore, in all cases where reference is made to an "oxidative conversion" in connection with embodiments of the invention, this is to be understood as an oxidative dehydrogenation of ethane.

The oxidative conversion advantageously takes place at a temperature of the catalyst in a range between 240 and 500° C., preferably between 280 and 450° C., in particular between 300 and 400° C.

One advantage is that the feed mixture is fed to the reactor at a pressure in a pressure range from 1 to 10 bar (abs.), in particular from 2 to 6 bar (abs.). This is therefore a process operating at comparatively low pressure, in which advantages of the invention arise in a particular way. A reduction of catalytically inactive material reduces the pressure loss in a corresponding reaction tube, which is particularly advantageous for corresponding "low pressure" processes.

One particular advantage is that within the scope of the invention, a water content in the feed mixture can be set which can be between 5 and 95% by volume, in particular between 10 and 50% by volume and further in particular between 14 and 35% by volume. As also disclosed, for example, in EP 3 558 910 B1 of the applicant, it is also possible, for example, to determine at least one parameter indicating an activity of the or one of the catalysts and, on this basis, to adjust an amount of water in the reaction feed stream on the basis of the at least one determined parameter.

In particular, an embodiment in which the feed mixture comprises ethane and in which the molar ratio of water to ethane in the feed mixture is at least 0.23 may be advantageous.

The invention can be applied independently of the guidance of the cooling medium (i.e. co-current or counter-current). If the cooling medium, in particular a molten salt, is fed in countercurrent, a particular additional advantage can be achieved, since here the reaction heat from the catalyst zones can be partially utilized, for example in a preheating zone. Likewise, different cooling circuits in combination with different catalyst layers are conceivable (as also indicated in more detail in WO 2019/243480 A1).

There is a particular advantage if the reactor is designed in such a way that the reactor is explicitly cooled differently in certain areas, i.e. there is the possibility of a separate cooling circuit (with possibly even different coolant flow directions). The advantage of this is a targeted temperature and thus activity adjustment in certain zones. This means that these zones can also be explicitly "switched on" by a corresponding heat input, for example, or "switched off" if not required or only required to a limited extent, by deliberately exceeding or falling below the start-up temperatures of the catalytically active materials.

In other words, in one embodiment, the invention proposes that the reaction tubes are cooled using one or more cooling media flowing around the reaction tubes. Different tube sections can thereby be cooled with particular advantage using different cooling media, the same cooling medium in different cooling medium circuits, and/or the same or different cooling media in different or the same flow directions.

The invention also extends to a plant for the production of a target compound comprising a tube bundle reactor having multiple reaction tubes arranged in parallel, said plant comprising means adapted to distribute a feed mixture containing ethane to the reaction tubes and to subject the ethane to an oxidative catalytic conversion in the reaction tubes, wherein successively arranged catalytic zones having different activity are provided for the catalytic conversion in the reaction tubes, and wherein one or more catalytically active materials and one or more catalytically inactive materials are provided in each of the catalytic zones.

According to the invention, the different activity of the catalytic zones is effected by providing the one or more catalytically active materials with identical basic formulation (i.e. also with identical elemental composition), wherein the one or more catalytically active materials is or are prepared using different calcination intensities.

For further features and advantages of the system proposed according to the invention, reference is expressly made to the above explanations. In corresponding embodiments, the system is set up in particular for carrying out a method as already explained above, also in various embodiments. The explanations apply accordingly.

Overall, as mentioned above, the invention creates a method for the targeted production of tailor-made catalysts (in particular with regard to their selectivity). A method for the preparation of catalytically active materials for use in the oxidative dehydrogenation of ethane may therefore also be an object of the invention. The method comprises providing catalyst components of the type explained above, in particular metals in the form of the aforementioned metal oxides, and subjecting them to catalyst synthesis, in particular hydrothermal synthesis, after preparing aqueous solutions or slurries, and subjecting a raw material obtained thereby to calcination under different calcination conditions. The different calcination conditions include, in particular, different calcination temperatures and/or calcination durations. The catalytically active materials obtained are introduced into catalysis zones of a reactor together with one or more catalytically inactive materials as a carrier or binder, the proportion of the one or more catalytically inactive materials being in particular essentially equal.

In this context, the invention comprises an improved manufacturing procedure of the catalytic active component of the catalyst, i.e. the active material of a catalyst (shaped body), in the form of using the pure oxides as raw materials. This leads to increased selectivity, for example to ethylene, already in the catalytic active component of the catalyst. Furthermore, a selective gradation of the catalyst activity is achieved by different calcination intensities, so that different layers of different activity can be generated via different calcination intensities. Overall, this enables the use of significantly less expensive raw materials that are available in the required quantities, as well as ensuring easy scalability of catalyst production on a technical scale.

The combination of catalysts produced in this way, in particular in an ODH(E) process with a reactor system with multiple reaction zones, leads to a significant increase in catalyst lifetimes as well as improved selectivities or product yields compared to a reactor system with multiple reaction zones known from the prior art, in which the reaction zones are formed by diluting the layers with inert material or diluting the catalyst shaped bodies themselves with inert components.

Overall, the invention allows a significant process intensification by using the specifically tailored catalysts or catalytically active materials in a reactor system with multiple reaction zones.

Embodiments

The invention is further explained below with reference to examples corresponding to embodiments of the invention and comparative examples not in accordance with the invention, as well as associated figures and tables.

The invention minimizes or avoids the use of inert material (catalytically inactive material) to dilute the active catalyst mass (catalytically active material). As explained and evidenced below, it is possible to produce tailor-made catalysts (hereinafter the term "catalyst" is used in particular for the catalytically active material) with a specifically adjusted conversion-selectivity behavior and a specifically adjusted activity per volume, so that they can be used in a particularly high-performance process, in particular for olefin production by means of oxidative dehydrogenation of alkanes, in particular of ethane.

As mentioned above, the invention makes use of the fact that the activity of a particular catalyst material can be influenced by its production. The catalytically active material itself remains in principle the same in terms of composition and can in particular be taken from the same synthesis approach. This surprising effect was found in a catalytic test of MoVNb(Te)O$_x$ catalyst material of the same synthesis approach and thus the same stoichiometry (element composition), but different calcination temperatures. As explained below, a significant (and in particular the only required) influencing factor is the calcination intensity, which results from calcination temperature and calcination duration.

The specific pore volume and/or BET surface area can serve as a characteristic feature for the catalytically active materials. These quantities are generally dependent on the parameters of the synthesis formulation, calcination intensity and composition.

Raw Materials and Synthesis Processes

In principle, different synthesis formulations, different calcination processes, different calcination intensities and different tellurium contents (in each case individually or in defined combination) could lead to the setting of different activities of catalytically active materials that can be used according to the invention.

Different synthesis formulations are known for the preparation of corresponding catalytically active materials. For example, a synthesis of MoVNbTe mixed oxide catalysts by combining solutions and spray drying and calcination is described in JP H07-053414 A. Significantly improved syntheses with very high content of the catalytically active M1 phase and thus higher selectivity and activity were subsequently described by hydrothermal synthesis in autoclaves from the soluble precursors (see, for example, A. Celaya Sanfiz et al, "Preparation of Phase-Pure M1 MoVTeNb Oxide Catalysts by Hydrothermal Synthesis-Influence of Reaction Parameters on Structure and Morphology", Top. Catal. 50, 2008, 1-32).

An alternative more recent synthesis method starts from the metal oxides of the respective metals instead of corresponding soluble compounds of the respective metals. Here, the metal oxides are subjected to hydrothermal synthesis in the presence of oxoligands, as indicated, for example, in DE 10 2017 000 861 A1. In this synthesis, crucial parameters are the temperature and heating method of the autoclave synthesis and the crystallization time. Thus, in DE 10 2017 000 861 A1 the crystallization in an autoclave with heating jacket is described, while similar syntheses with other raw materials to MoVNbTe catalysts with M1 phase at 175° C. in microwave heating are described (for example WO 2013/021034 A1). It is also described that the length of the synthesis time in the autoclave can also influence the activity of the catalyst. For example, maximum activity (but not maximum selectivity) can be achieved after 3.5 hours of synthesis time (see D. Melzer et al, "Design and synthesis of highly active MoVTeNb-oxides for ethane oxidative dehydrogenation," Nature Commun. 10, 2019, 4012, FIG. 11).

It should be possible to produce an economically viable catalyst from precursors that are commercially available in large quantities and at the lowest possible prices. For the elements Mo, V, Nb and Te, these are the metal oxides MoO$_3$, V$_2$O$_5$, Nb$_2$O$_5$ and TeO$_2$. Therefore, previous fabrication specifications of MoVNbTeO$_x$ materials based on the (water) soluble precursors of the metals, such as ammonium heptamolybdate or vanadyl sulfate, are less advantageous. Furthermore, it is advantageous to replace telluric acid, which is soluble but not commercially available in large quantities, i.e. it is an advantage to use tellurium oxide, as described in DE 10 2017 000 848 A1 (Example 2).

In Example 2 of DE 10 2017 000 848 A1, 3.3 L distilled water was introduced into an autoclave (40 L). Water was added and heated to 80° C. with stirring. Meanwhile, 725.58 g of ammonium heptamolybdate tetrahydrate was added and dissolved (hereafter referred to as AHM solution). In two beakers, each with a volume of 5 L, 1.65 L dist. Water was also heated to 80° C. with stirring on a magnetic stirrer with temperature control. To each of these beakers, 405.10 g of vanadyl sulfate hydrate (V content: 21.2%) and 185.59 g of ammonium nioboxalate (Nb content: 20.6%) were then added and dissolved (hereafter referred to as V solution and Nb solution). 65.59 g TeO$_2$ was dissolved for 3 h the previous day in 200 g dist. Water using a ball mill and transferred to a beaker with 1.45 L dist. Water into a beaker (hereafter referred to as Te suspension). The V solution was successively pumped into the AHM solution, then the Te suspension ground the previous day was added, stirring continued for 1 h at 80° C., and finally the Nb solution was pumped into the AHM solution using a peristaltic pump. The pumping time was 5 min at 290 rpm (tube diameter 8×5 mm) for the V solution and 5 min at 275 rpm (tube diameter 8×5 mm) for the Nb solution. The resulting suspension was now stirred further at 80° C. for 10 min, and the stirrer speed during precipitation was 90 rpm. Subsequently, nitrogen was superimposed by building up a pressure in the autoclave with nitrogen up to about 6 bar and opening the drain valve until nitrogen flowed through the autoclave under pressure (5 min). At the end, the pressure was released again, via the vent valve, down to 1 bar residual pressure. Hydrothermal synthesis in the autoclave was carried out at 175° C. for 20 h (heating time 3 h) with an anchor stirrer, at a stirrer speed of 90 rpm. After synthesis, filtration was performed using a vacuum pump with a blue sand filter and the filter cake was washed with 5 L dist. Water. Drying was carried out at 80° C. in a drying oven for 3 days and then grinding was carried out in an impact mill, achieving a solid yield of 0.8 kg. Calcination was carried out at 280° C. for 4 h in an air stream (heating rate 5° C./min, air volume 1 L/min). Activation was carried out in the retort at 600° C. for 2 h in a nitrogen stream (heating rate 5° C./min, nitrogen flow rate 0.5 L/min).

A particularly advantageous basic preparation process for a catalyst from the metal oxides is, due to its economy, that described in DE 10 2017 000 861 A1 (Example 1), which has also already been mentioned. It leads to an exemplary catalyst with the stoichiometry MoV$_{0.3}$Nb$_{0.1}$Te$_{0.1}$O$_x$. Within the scope of the invention, the catalyst material can be prepared in principle as described in the aforementioned example of DE 10 2017 000 861 A1. In doing so, the respective suitable metal oxides can be subjected to hydrothermal synthesis.

In the method used in Example 1 of DE 10 2017 000 861 A1, TeO$_2$ was slurried in 200 g of distilled water and ground in a planetary ball mill with balls of 1 cm diameter (ZrO$_2$). The portion was then transferred to a beaker with 500 mL of distilled water. Nb$_2$O$_5$ was slurried in 200 g of distilled water and ground in the same ball mill. The portion was then transferred to a beaker with 500 mL of distilled water. The next morning, the temperature was heated to 80° C., 107.8 g of oxalic acid dihydrate was added to the Nb$_2$O$_5$ suspension, and stirred for about 1 h. The mixture was then mixed with water. In the autoclave (40 L), 6 L of distilled water was placed and heated to 80° C. with stirring (stirrer speed 90 rpm). When the water reached the temperature, 61.58 g of citric acid, 19.9 g of ethylene glycol, 615.5 g of $MoO_3$, 124.5 g of $V_2O_5$, the ground $TeO_2$ and the ground $Nb_2O_5$ in oxalic acid were added successively. 850 mL of distilled water was used to transfer and rinse the vessels. The complete volume of water in the autoclave was 8.25 L. Nitrogen was then added to the overlay. Hydrothermal synthesis was carried out in a 40-L autoclave at 190° C./48 h. The synthesis was carried out in a 40-L autoclave. After the synthesis, filtering was performed using a vacuum pump with blue sand filter and the filter cake was washed with 5 L of distilled water.

Drying was carried out at 80° C. in a drying oven for 3 days and then the product was ground in an impact mill. A solid yield of 0.8 kg was achieved. Subsequent precalcination was carried out at 280° C. for 4 h in air (heating rate 5° C./min air: 1 L/min). Activation or calcination was carried out in a retort at 600° C. for 2 h (heating rate 5° C./min nitrogen: 0.5 L/min).

For example, and in particular via a reduction of the content of tellurium in the catalytically active material, the activity can be further increased, as described in WO 2018/141652 A1 and in Melzer et al (see above).

Test Facilities

In the context of the examples explained below, different test plants were used, which are explained below at the outset.

In the test plant designated "Test Plant 1", an experimental reactor designed as a double tube (fixed bed, max. total length of the bed 0.9 m, inner diameter of the reaction chamber 10 mm) was used. The heating or cooling is carried out with the aid of a thermal oil bath, whereby the thermal oil is pumped through the outer space of the reactor and thus heats the inner space or the reaction zone or cools it at the same time (the reaction is an exothermic reaction).

The test plant, designated "Test plant 2", comprises a tubular reactor with a usable length of 1 m and an internal diameter of 25 mm. Heating, or at the same time also cooling, was carried out by means of a salt bath in which the reactor is immersed. For technical reasons, air was used as oxidant instead of pure oxygen. Furthermore, this test plant 2 could only be operated under atmospheric pressure. The other test conditions included a catalyst amount of 337 g, a reaction feed composition of ethane to nitrogen to oxygen to water (vapor) of 11.1 to 46.7 to 6.8 to 35.4 (mol % each), GHSV of 412 (NLgas/h)/Lcatalyst. The test results are shown in Table 4.

Example 1—Influence of the Basic Formulation on the Activity-Selectivity Behavior A catalyst designated "Catalyst A" was thereby prepared on the basis of the soluble precursors and $TeO_2$ (basically as described in Example 2 of DE 10 2017 000 848 A1 described above). A catalyst designated "Catalyst B" was produced on the basis of the metal oxides (basically as described in Example 1 of DE 10 2017 000 861, see above).

The test was carried out in the previously described test facility 1. The exact test conditions are listed in Table 1 below. The different activities are summarized in Table 2.

TABLE 1

| | A | B1 | B2 |
| --- | --- | --- | --- |
| | Conditions/Test point | | |
| | | Catalyst | |
| | Catalyst A | Catalyst B | |
| Catalyst mass [g] | | 48.02 | |
| Proportion of binder [wt. %] | | 10 | |
| Catalyst shape | Quartered 3 × 3 mm tablets | | |
| System pressure [bara] | | 3.5 | |
| WHSV [$g_{C2H6}/(g_{cat}*h)$] | | 0.8 | |
| Oil temperature [° C.] | 298 | 298 | 307.7 |
| Mean catalyst bed temperature [° C.] | 317.7 | 310.0 | 323.7 |
| $O_2/C_2H_6$ [mol/mol] | 0.373 | 0.373 | |
| $H_2O/C_2H_6$ [mol/mol] | 0.234 | 0.286 | |
| Feed composition [mol %] | 61.4 | 60.6 | |
| $C_2H_6$ | | | |
| $O_2$ | 24.2 | 22.0 | |
| $H_2O$ | 14.4 | 17.4 | |

TABLE 2

| | A/Cat. A | B1/Cat. B |
| --- | --- | --- |
| | Conditions/test point | |
| Catalyst activity [$g_{C2H6-turnover}/(g_{Kat} × h)$] | 0.378 | 0.305 |
| Relative catalyst activity [%] | 100 | 81 |

Catalyst B showed about 19% lower activity than catalyst A, i.e. there is a lower ethane conversion at the same catalyst bed inlet temperature or the same coolant temperature. The activity test was performed at the same coolant temperature (oil bath temperature) of 298° C. (see Table 1).

Figure 1A:
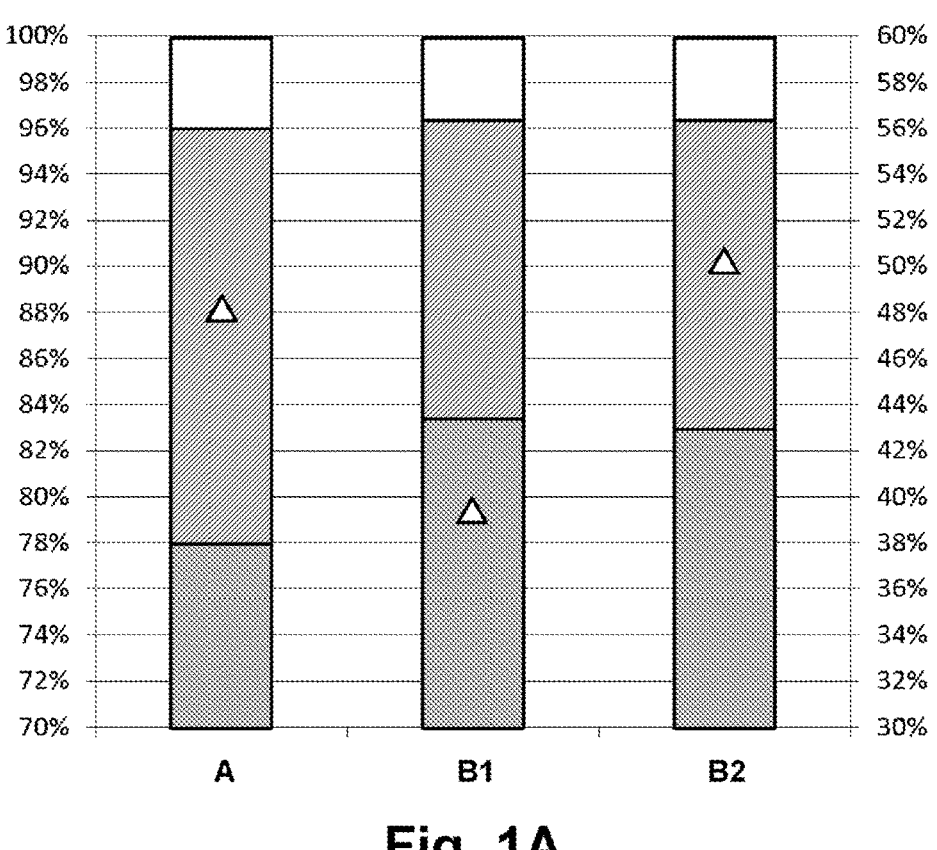
FIG. 1A illustrates selectivities and conversions obtained with catalysts according to embodiments of the invention.

At the same conversion, catalyst B based on the pure oxides exhibits a higher selectivity to ethylene and acetic acid than catalyst A based on the soluble precursors and $TeO_2$ with the same total selectivity of over 96% to the commercial value products ethylene and acetic acid, the selectivity to ethylene being about 5% points higher (and the selectivity to acetic acid being corresponding 5% points lower), namely approximately 83% versus approximately 78% selectivity to ethylene (catalyst B versus catalyst A) and approximately 13% versus approximately 18% selectivity to acetic acid (catalyst B versus catalyst A). This fact is illustrated in FIG. 1A, which shows the selectivities (left vertical axis; cross-hatching: ethylene, diagonal hatching: acetic acid, without filling: carbon oxides) and conversions (right vertical axis; triangles) of the catalysts according to the test points A, B1 and B2 shown in Table 1.

To achieve the same conversion, a higher catalyst bed inlet temperature and also a higher average or minimum catalyst bed temperature is required due to the lower activity of a catalyst B prepared using the pure oxides. Finally, the increased average catalyst bed temperature is also the reason for the observed increased selectivity to ethylene. The explanation for this can be found, for example, in WO 2019/243480 A1 on page 13, line 4 to page 14, line 2.

Figure 1B:
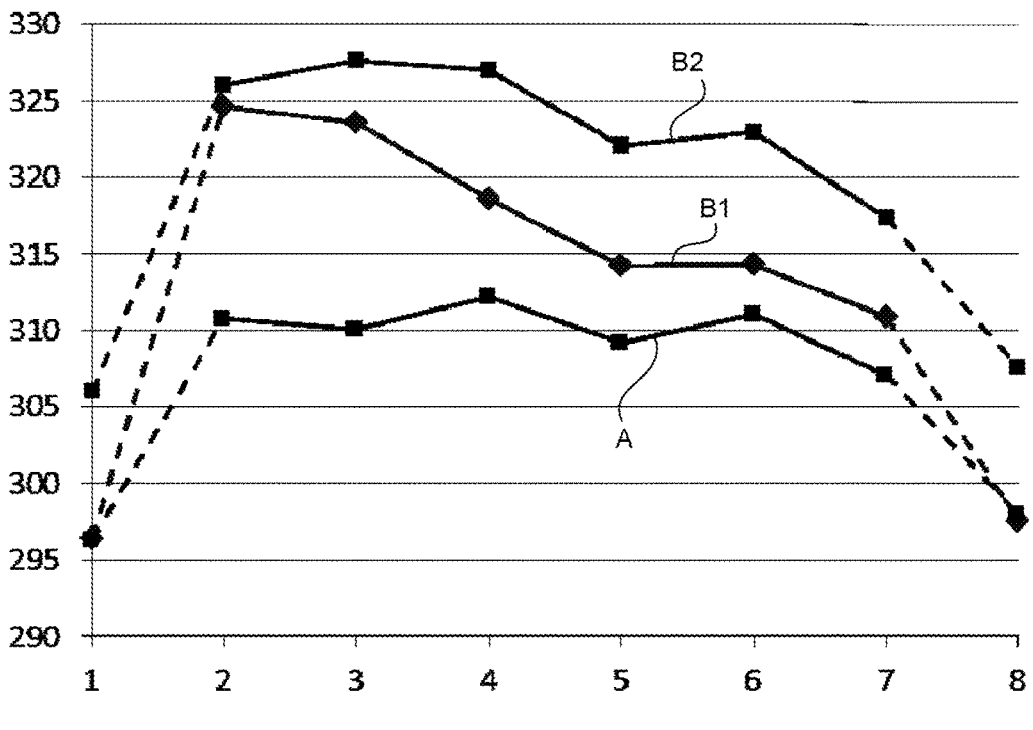
FIG. 1B illustrates temperature profiles obtained with catalysts according to embodiments of the invention.

There is a flatter temperature profile (even at higher catalyst bed entry temperature) of catalyst B versus catalyst A due to lower activity and lower selectivity to acetic acid. An explanation can be found in the fact that the ethane oxidation to acetic acid is significantly more exothermic than the ethane to ethylene oxidation (standard reaction enthalpy ethane to ethylene –105 kJ/mol, standard reaction enthalpy ethane to acetic acid —590 kJ/mol). This effect can reduce the risk of thermal runaway of the catalyst bed or a part of the catalyst bed or a reaction zone in a commercial reactor. This circumstance is illustrated in FIG. 1B, in which the corresponding temperatures in ° C. on the vertical axis are plotted for measuring points before (measuring point 1) and after (measuring point 8) a catalyst bed of approximately 60 cm as well as measuring points (measuring points 2 to 7) within the catalyst bed on the horizontal axis.

To achieve the same conversion, a higher catalyst bed inlet temperature and also a higher average or minimum catalyst bed temperature is required due to the lower activity of a catalyst B prepared over the pure oxides. Finally, the increased average catalyst bed temperature is also the reason for the observed increased selectivity to ethylene. A possible explanation for this can be found, without being bound by this, in WO 2019/243480 A1, page 13, line 4 to page 14, line 2.

Surprisingly, the supposed disadvantage of a lower activity of a catalyst prepared via the pure oxides therefore turns out to be particularly advantageous in the sense of the invention, since the reduced activity means that the process can or should/must be operated at somewhat elevated temperatures, which in the sense of the explanation from WO 2019/243480 A1 (see above) then leads to an increased yield of the particularly preferred value product ethylene.

Example 2—Influence of Calcination Conditions

As described above, the basic formulation decisively influences the conversion-selectivity behavior. However, the activity of a catalyst can be adjusted within a basic formulation by selecting suitable calcination conditions (calcination intensity). The calcination conditions include in particular the selection of the calcination process technology, i.e. continuous or discontinuous calcination, and the selection of the calcination intensity (which is in particular due to calcination temperature and calcination time).

Surprisingly, it was found that the calcination intensity has a decisive influence on the activity of a catalyst. For a given calcination temperature, the calcination intensity is determined in particular by the length of the heating, holding and cooling times. Furthermore, an existing or non-existing mixing of the calcination material as well as the layer thickness of the calcination material (e.g. filling level in a calcination tray in the case of discontinuous calcination or the layer thickness forming in the case of continuous mixing in the case of continuous calcination) also play a role.

It can thus be expected that the calcination intensity is also largely determined by the choice of calcination process technology, i.e. in a discontinuous manner, such as in a retort or muffle furnace, or in a continuous manner, such as in a rotary kiln. In discontinuous calcination, the calcination material usually cannot be mixed. Furthermore, the heating, holding and cooling times are longer in a discontinuous calcination than in a continuous calcination. A continuous calcination, especially in a rotary kiln, is characterized by the fact that the calcination material is also mixed simultaneously during calcination due to the forward transport of the calcination material through the tube rotating about its longitudinal axis, which in particular also means a more uniform treatment of the calcination material. The calcination time, i.e. the overall heating, holding and cooling times, is much shorter in a continuous calcination, especially in a rotary kiln: the heating phase is very short and takes place only in a small part at the beginning of the (rotary) tube kiln. The holding time is mainly characterized by the kiln length and the transport speed (for example influenced by the kiln inclination in the case of a rotary kiln). The cooling time is minimal because the material is transferred from the hot kiln directly to a collecting vessel at ambient or room temperature. Thus, in discontinuous calcination, the calcination material generally experiences a significantly higher calcination intensity.

At this point it should be expressly noted that the calcination intensity should generally be selected in a way that the calcination material can form corresponding stable crystal phases. In the case of catalysts or catalyst materials, this means particularly a sufficient crystal phase stability with regard to the reaction or catalysis conditions, especially with regards to the temperatures prevailing during catalysis, which is expressed in a constant activity and selectivity for the intended reaction.

An adapted calcination intensity (time and temperature), in particular the choice of calcination temperature T (see examples below), thus contributes significantly to the properties of the catalytically active materials mentioned above, whereby particular attention must be paid to homogeneous calcination under inert gas. Homogeneous calcination in small quantities is also possible in a pan in the furnace, but for large quantities and thick powder layers, the calcination intensity is less homogeneous. For large quantities, it is therefore necessary to move the material, e.g. in a rotary kiln. It should be noted that a normal kiln requires a certain amount of time to cool down before the material is removed. In a rotary kiln, on the other hand, the material falls directly from the hot tube into a cold container, and therefore reproducible and precisely definable conditions can be set. On the other hand, extremely long calcination times cannot be achieved with the usual technical tube lengths of a rotary kiln. To a limited extent, therefore, a shorter residence time in a continuous kiln, such as a rotary kiln, can be replaced by a higher calcination temperature. Therefore, the calcination intensity resulting from time and temperature is decisive here.

Example 2a—Influence of Calcination Process Technology and Calcination Time

This effect was shown when testing two catalyst samples prepared in exactly the same way using the same basic formulation, i.e. starting from the insoluble oxides (see above). The only difference is in the choice of calcination process technology and thus calcination intensity. A catalyst designated "Catalyst C" was discontinuously calcined in a muffle furnace. A catalyst designated "Catalyst D" was calcined in a rotary kiln. As mentioned above, calcination in a muffle furnace is a discontinuous process, while calcination in a rotary kiln is a continuous process. The calcination temperatures (i.e. the temperatures during the holding time) were the same for both calcination processes, namely 650° C., but the effects described above result in corresponding effects on the respective calcination intensity, i.e. a higher calcination intensity in the case of catalyst C and a significantly lower calcination intensity compared to catalyst C in the case of catalyst D, due to the mode of operation. The sufficient calcination intensity for catalyst D was confirmed by a consistent catalyst performance over a longer period of time.

The testing of the catalyst samples Catalyst C and Catalyst D obtained via different calcination intensities was carried out in the above-described test plant 1 under exactly the same conditions for both samples (with regard to filled catalyst quantity, system pressure, composition of the reaction feed). The comparison of the activities at 295° C. oil bath temperature (simultaneously corresponding to the catalyst bed inlet temperature) is shown in Table 3.

Based on the data from Table 3, it can be seen that discontinuous calcination results in a catalyst with a lower activity, because this discontinuous calcination, carried out in the retort, is associated with a stronger calcination intensity, in the form of a longer effective calcination time (including heating and cooling phases at the same temperature of 650° C. during the holding time).

TABLE 3

| | Catalyst sample | |
| --- | --- | --- |
| | Catalyst C | Catalyst D |
| Calcination Process Engineering | Discontinuous | Continuous |
| Calcination temp. of catalyst [° C.] | 650 | 650 |
| Calcination time (holding time) | 2 h | 0.5 h |
| Specific pore volume [cm³/g] * | 0.032 | 0.041 |
| Reaction temperature [° C.] | 295 | 295 |
| Ethane turnover | 35.2 | 39.6 |
| Activity [mol$_{C2H6\text{-}turnover}$/(L$_{cat}$*h)] | 9.96 | 11.08 |
| Rel. activity [%] (related to Cat. D) | 89.9 | 100 |

The value marked with an asterisk * (the same applies to the following tables) refers to the pure MoVNbTe oxide catalyst powder (before tabletting). For tabletting, silica and wax are added as tabletting excipients, with the wax being burned out as mentioned above. The porosity of the silica co-determines the porosity of the final catalyst shaped bodies, which means that it differs. However, the specific pore volume of the actual catalyst powder correlates with the activity.

The same behavior is obtained for catalysts E and F. The testing of catalyst samples was carried out in test plant 2 described above. The other test conditions for testing catalysts E and F in test plant 2 included a catalyst amount of 337 g, a reaction feed composition of ethane to nitrogen to oxygen to water (vapor) of 11.1 to 46.7 to 6.8 to 35.4 (mol % each), GHSV of 412 (NL$_{Gas}$/h)/L$_{catalyst}$. The test results are shown in Table 4.

It is clear from Table 4 that a catalyst prepared via discontinuous calcination, referred to here as "Catalyst E", i.e. the catalyst which was subject to a higher calcination intensity, has a lower activity than a catalyst designated "Catalyst F", which was prepared via continuous calcination and was thus subject to a lower calcination intensity. The lower activity of catalyst E compared to catalyst F can be seen from the fact that catalyst E required a 4 K higher reaction temperature to achieve the same ethane conversion.

TABLE 4

| | Catalyst sample | |
| --- | --- | --- |
| | Catalyst E | Catalyst F |
| Calcination Process Engineering | Discontinuous | Continuous |
| Calcination temperature of the catalyst [° C.]. | 650 | 650 |
| Calcination time (holding time) | 2 h | 0.66 h |
| Specific pore volume [cm³/g] * | 0.033 | 0.039 |
| Reaction temperature (corresponds to salt bath temperature) [° C.]. | 326 | 322 |
| Ethane conversion [%] | 67.1 | 67.1 |

Example 2b—Influence of Calcination Temperature

As described above, the basic formulation decisively influences the conversion-selectivity behavior. However, the activity and thus also the start-up temperature of a catalyst can be adjusted within a basic formulation by selecting suitable calcination conditions.

This effect was found in a catalytic test of MoVNbTeO$_x$ catalyst material of the same synthesis approach and thus the same stoichiometry (element composition), i.e. the identical basic formulation, however, different calcination temperatures but the same calcination times.

The MoVTeNbO$_x$ materials were prepared as described in DE 10 2017 000 861 (Example 2), except that the activation under inert gas was not carried out in a retort at 600° C. as in the section there [0049], but in a rotary kiln of 10 cm diameter and one meter heated length with a residence time of 30 min, and an inlet temperature of 550° C. and with an outlet temperature given as calcination temperature in Table 5.

TABLE 5

| | Catalyst sample | | |
| --- | --- | --- | --- |
| | Catalyst G | Catalyst D | Catalyst H |
| Calcination technology | Continuous | Continuous | Continuous |
| Calcination temperature [° C.] | 630 | 650 | 670 |
| Calcination time | 0.5 h | 0.5 h | 0.5 h |
| Spec. pore volume [cm³/g]* | 0.0533 | 0.041 | 0.0293 |
| Reaction temp. window [° C.] | 230-295 | 270-300.5 | 295-310 |
| Ethane conversion range measured for reaction temp. window [%] | 4.4-47.5 | 17.9-46.2 | 30.0-43.9 |
| Number of different temperature levels | 8 | 4 | 4 |
| Start-up temperature [° C.] (calculated) = temperature for 10% ethane conversion | 251.0 | 255.7 | 260.0 |

The catalysts prepared in this way (catalysts "G", "D" and "H") were tested in the above-described test plant 1 under exactly the same conditions (amount of catalyst filled in, system pressure, composition of the reaction feed) with regard to their activity. At an oil bath temperature of 295° C., clear absolute and relative activity gradations of +21% and −23% (relative in each case) were found for the differently calcination catalysts compared with the basecase (standard calcination temperature of 650° C.).

An Arrhenius plot, i.e. a plot of the natural logarithm of the reaction rate constant against the reciprocal of the reaction temperature (in Kelvin), can be made for each of the catalyst samples to determine the start-up temperature listed in Table 5. The creation of an Arrhenius plot is in principal known to the person skilled in the art.

The Arrhenius plot provides a straight line with different parameters (slope and intercept) for each of the catalyst samples. With the aid of the respective straight line equation, the corresponding reaction rate constant can be determined for a given ethane conversion and, via this, the corresponding reaction temperature. The corresponding reaction temperature determined for an ethane conversion of 10% is given in the line "Start-up temperature [° C.] (calculated) =temperature for 10% ethane conversion" in Table 5.

Based on the observed trend in the activities and the start-up temperatures of catalysts G, D and H as a function of the calcination temperature (cf. FIG. 2 and Table 5), it can be assumed that the activity of the catalysts can be further increased with lower calcination temperatures, at least within certain limits, as long as the temperature and duration of the calcination, i.e. the calcination intensity, is sufficient for the formation of a solid or crystal phase which is sufficiently stable for catalysis purposes. In fact, a further, significant increase in activity and thus further, significant shift in the start-up temperature to lower values was observed for a catalyst that had been calcined (discontinuously) at 400° C. instead of 650° C. ("Catalyst I", see Table 6).

This catalyst was tested in test plant 2 under the test parameters specified above for test plant 2. For comparison, catalyst F (cf. Table 4) was also tested in this test plant 2 under the same conditions. The test results are shown in Table 6.

TABLE 6

| | Catalyst sample | | |
|---|---|---|---|
| | Catalyst F | | Catalyst I |
| Calcination temperature of the catalyst [° C.]. | 650 | | 400 |
| Specific pore volume [cm³/g]* | 0.039 | | 0.11 |
| Salt bath temperature [° C.] | 310 | 322 | 302 |
| Ethane turnover | 53.0 | 67.1 | 64.2 |

A significantly higher activity of catalyst I compared to catalyst F (cf. also Table 4) is proven from the direct experimental comparison in test plant 2 (cf. Table 6): Catalyst F exhibits an ethane conversion of about 67% at a salt bath temperature of 322° C. Catalyst I, on the other hand, only requires a salt bath temperature of 302° C. for a conversion of 64% and still exhibits a significantly higher conversion at this temperature than Catalyst F at a higher temperature of 310° C. (ethane conversion Catalyst F of 53%).

In order to estimate the start-up temperature of Catalyst I under the technically much more relevant conditions of test plant 1, the following procedure was followed: using the ethane conversion determined at the salt bath temperature given in Table 6 and the other test conditions given, a reaction rate constant corresponding to this temperature was calculated. The procedure for this is in principal known to the person skilled in the art.

This reaction rate constant served as the starting point for determining a corresponding Arrhenius straight line. Since only one measuring point was available for Catalyst I, the same slope of the Arrhenius straight line was used as was determined for the test conditions from test plant 1 (cf. results from FIG. 2 and Table 5), assuming that the apparent activation energy is independent of the test conditions. With the aid of this Arrhenius straight line determined for catalyst I, and taking into account the inaccuracy resulting from this procedure, a resulting range for the start-up temperature of catalyst I of approximately 233 to 242° C. was estimated for the technically relevant test conditions of test plant 1. Despite the relatively high uncertainty with regard to the start-up temperature for catalyst I under the technically relevant conditions, it can be seen that the range of the start-up temperature for catalyst I is clearly below the start-up temperature of catalyst G (cf. Table 5), correspondingly catalyst I also exhibits the highest activity among the catalysts tested. Thus, the following activity series can be established (in decreasing order): Catalyst I>Catalyst G>Catalyst D>Catalyst H.

Example 2c—Conversion-Selectivity Behavior

Surprisingly, however, it is shown that catalysts of a basic formulation exhibit almost the same conversion-selectivity behavior irrespective of the selected calcination process technology or calcination intensity (cf. Table 7).

TABLE 7

| | Cat. C | Cat. D | Cat. D | Cat. G |
|---|---|---|---|---|
| Calcination process | discount. | cont. | cont. | cont. |
| Calcination temperature [° C.] | 650 | 650 | 650 | 630 |
| Reaction temperature (corresponds to salt bath temperature) [° C.] | 295 | 290 | 295 | 290 |
| Turnover $C_2H_6$ [%] | 35.0 | 34.1 | 39.6 | 40.2 |
| Selectivity $C_2H_4$ [%] | 81.9 | 81.8 | 81.6 | 81.6 |
| Selectivity AcOH [%] | 14.5 | 14.5 | 14.2 | 14.3 |

This is confirmed for catalyst samples originating from one and the same autoclave synthesis approach (catalyst D and G) as well as from different autoclave synthesis approaches (catalyst C). Thus, catalysts of a certain activity can be used selectively in a reactor or a reaction zone of a reactor or a respective reactor tube of a shell-and-tube reactor, for example, in order to achieve an optimum activity of the catalyst bed and thus optimum balance between heat production by reaction and heat removal within a reactor or within a reaction zone of a reactor or reactor tube, and thus to maximize the productivity of a commercial reactor or to make optimal use of the reactor.

Table 7 emphasizes in addition the above-mentioned observations on the activity depending on the different calcination intensities. According to what has been described above, the gradation of calcination intensity in Table 7 is in descending order (from the highest to the lowest calcination intensity): Calcination Intensity Catalyst C>Calcination Intensity Catalyst D>Calcination Intensity Catalyst G. Accordingly, the activity increases in the reverse order, i.e. Activity Catalyst C<Activity Catalyst D<Activity Catalyst G. This can be seen by comparing the conversions at the corresponding reaction temperatures: for a similar ethane conversion of about 34 to 35%, a reaction temperature 5 K higher is required for Catalyst C compared to Catalyst D. The reaction temperature of Catalyst D is 5 K higher than that of Catalyst C. The reaction temperature of Catalyst D is 5 K higher. Catalyst G, in turn, is more active than catalyst D, because for an ethane conversion of about 40%, a 5 K lower reaction temperature is required for catalyst G compared with catalyst D. The above-mentioned independence of selectivity from calcination intensity for catalysts of the same basic formulation is confirmed by almost identical selectivity values at comparable conversion levels of about 34 to 35% for catalysts C and D and of about 40% for catalysts D and G. It should be mentioned here that deviations in the selectivities of up to 0.3% points are not to be regarded as significantly different (error analysis based on ten independent repeat measurements on catalyst G).

Example 3—Plant and Reactor

Figure 2:
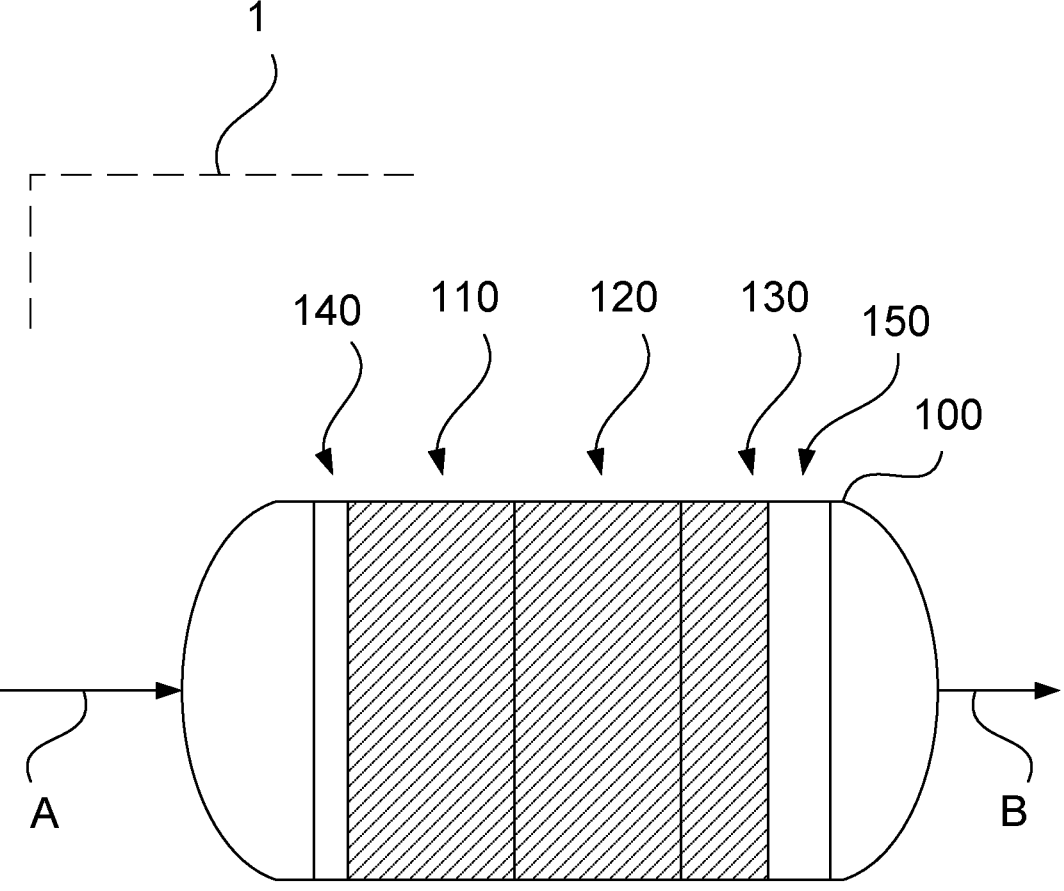
FIG. 2 illustrates a plant according to one embodiment of the invention in simplified schematic view.

FIG. 2 illustrates a plant for the production of olefins according to one embodiment of the invention in the form of a highly simplified plant diagram and is designated overall as 1. Plant 1 is shown only schematically. In particular, the basic arrangement of the catalytic zones in a shell-and-tube reactor 100 is shown. Although a plant 1 for ODHE is described below, as mentioned above the invention is also suitable for use in the ODH of higher hydrocarbons. The following explanations apply to this case accordingly.

As mentioned, plant 1 has a shell-and-tube reactor 100 to which, in the example shown, a feed mixture A containing ethane and obtained in any manner is fed. The feed mixture A may contain, for example, hydrocarbons taken from a rectification unit not shown. The feed mixture A may also be, for example, preheated and otherwise processed. The feed mixture A may already include oxygen and, optionally, a reaction moderator such as steam, but corresponding media may also be added upstream or in the shell-and-tube reactor 100, as not shown separately. A product mixture B is removed from the tubular reactor 100.

Figure 3:
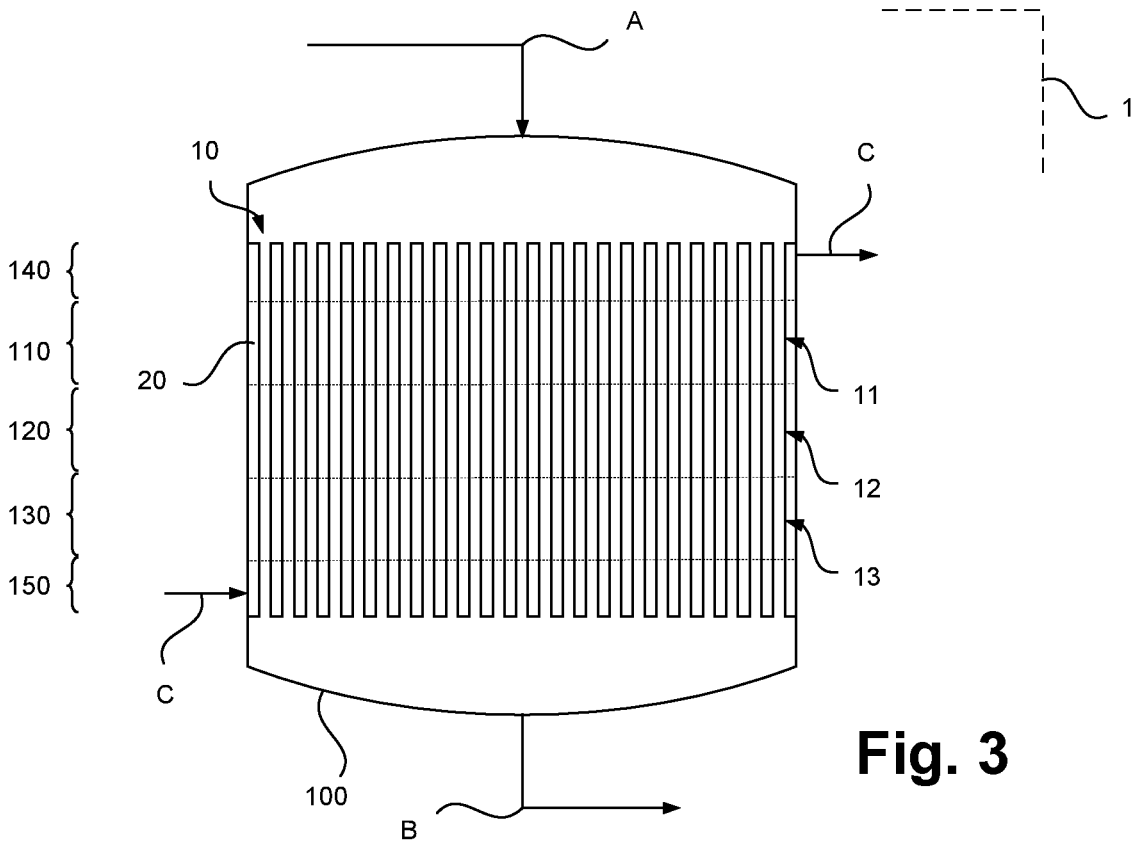
FIG. 3 illustrates a reactor according to one embodiment of the invention in simplified schematic view.

The shell-and-tube reactor 100, shown in detail in FIG. 3, has multiple parallel reaction tubes 10 (only partially labeled) extending through multiple reaction zones 110, 120, 130, three in the example shown. Upstream and downstream, respectively, a preheating zone 140 and a postreaction zone 150 may be present. The reaction tubes 10 are surrounded by a jacket region 20 through which, in the example mentioned, a coolant C of the type explained is passed. The illustration is greatly simplified because, as mentioned, reaction tubes 10 may be cooled using multiple cooling media flowing around reaction tubes 10, or different tube sections may be cooled using different cooling media, the same cooling media in different cooling media circuits, and/or the same or different cooling media in the same or different flow directions.

After being fed into the shell-and-tube reactor, the feed mixture A is distributed in a suitable manner to reaction tubes 10 at a temperature in a first temperature range. The reaction tubes have respective catalysis zones 11, 12 and 13 located in reaction zones 110, 120 and 130.

A catalytic conversion is effected by means of catalysis zones 11, 12 and 13 having different activity and arranged in series in reaction tubes 10, and wherein one or more catalytically active materials and one or more catalytically inactive materials are provided in each of the catalysis zones 11, 12 and 13. As explained, the different activity of the catalysis zones 11, 12 and 13 is effected by providing the one or more catalytically active materials having identical elemental composition and different activity.

FIG. 4 illustrates the production of a catalytically active material according to one embodiment of the invention in a simplified schematic representation or in the form of a schematic flow chart of a corresponding process 400.

The method comprises in particular manufacturing steps 410, 420 and 430, previously referred to as "first manufacturing steps", a subsequent calcination 440, and one or more subsequent manufacturing steps 450, previously referred to as "second manufacturing steps". Manufacturing step 410 represents in particular a suitable pretreatment of the feedstocks used, which is followed by a synthesis, for example an autoclave synthesis with crystallization (and, if necessary, filtration) in step 420. Step 430 may in particular comprise drying. Step 450 comprises, in particular, shaping, including any necessary burnout of the wax as previously explained.

The term "formulation" used, for example, in WO 2019/ 243 480 A1 has already been defined above and comprises in particular steps 410 to 440. Here, these steps 410 to 440 up to and including calcination 440 are thus carried out identically or essentially identically. A catalytically active material with exactly one defined elemental composition, exactly one set of physicochemical properties (e.g. BET surface area and/or nitrogen pore volume) and therefore a specific activity is produced. The process chain up to and including calcination 440 therefore mainly determines the activity of the finished catalyst shaped (with the same binder content).

In this context, the term "basic formulation", which was also defined previously, includes identical or essentially identical steps 410 to 430 up to and including drying, but not necessarily identical or essentially identical calcination 440. In this way, a precursor or base material with a precisely defined element composition is produced. However, this material must still be subjected to activation in the sense of calcination under nitrogen at temperatures of at least 400° C. so that the material is converted into the final catalytically active form. Different calcination intensities can be used here.

An activity setting made in embodiments of the invention for the respective catalyst layers can be influenced by specific selection of the calcination conditions or, more precisely, the calcination intensity. Although the catalytically active materials formed may have the same chemical or elemental composition ("chemically identical"), they differ in terms of their physicochemical properties, namely at least in terms of BET surface area and/or nitrogen pore volume. The calcination intensity thus determines the physicochemical properties or the materials are different with regard to these properties.

In step 450, activity can be graded by adding different proportions of binder during shaping. The different catalytic layers are then characterized by different proportions of binder. Thus, in absolute terms, the element composition is different for each catalytic layer (although the relative amounts of the catalytically active metals to each other do not change, since these are the same for all layers).

The invention claimed is:

1. A method for oxidatively dehydrogenating ethane to ethylene, comprising:
   distributing an ethane-containing feed mixture to multiple parallel reaction tubes of a shell-and-tube reactor; and
   subjecting the ethane-containing feed mixture to an oxidative catalytic reaction of the ethane in the reaction tubes, wherein;
      the catalytic reaction is carried out by means of catalysis zones having different activities and arranged in series in the reaction tubes; and
      one or more catalytically active materials and one or more catalytically inactive materials are provided in the catalysis zones;
   wherein the different activity of the catalysis zones is effected by providing the one or more catalytically active materials with identical or essentially identical basic formulation, the one or more catalytically active materials being prepared using different calcination intensities.

2. The method of claim 1, wherein the multiple catalytic materials have essentially the same conversion-selectivity behavior.

3. The method of claim 2, wherein a proportion of the one or more catalytically inactive materials in the respective catalysis zones to a total charge of the respective catalysis zones differs by no more than 25% relative to each other.

4. The method of claim 1, wherein the one or at least one of the multiple catalytically active materials comprises at least the metals molybdenum, vanadium, and niobium.

5. The method of claim 4, wherein the one or more of the catalytically active materials is made at least in part from the oxides of the metals.

6. The method of claim 1, in which a pore volume and/or a BET surface area in at least two of the catalysis zones differ from one another by 15 to 60% and the pore volume is used as a measure of the catalyst activity.

7. The method of claim 1, in which the oxidative reaction is carried out at a temperature of the catalyst in a range between 240 and 500° C. and/or in which the feed mixture is fed to the reactor at a pressure in a pressure range from 1 to 10 bar (abs.).

8. The method of claim 1, in which the feed mixture contains a water content which is adjusted between 5 and 95% by volume.

9. The method of claim 8, wherein the feed mixture comprises ethane and wherein the molar ratio of water to ethane in the feed mixture is at least 0.23.

10. The method of claim 1, wherein one or more cooling media is fed to the reactor whereby the reaction tubes are cooled via the one or more cooling media flowing around the reaction tubes.

11. The method of claim 10, wherein tube sections of the reaction tubes are cooled using different cooling media, the same cooling medium in different cooling medium circuits, and/or the same or different cooling media in different or the same flow directions.

12. A plant for oxidatively dehydrogenating ethane to ethylene, comprising:

a shell-and-tube reactor having multiple reaction tubes arranged in parallel;

means adapted to distribute a feed mixture containing ethane to the reaction tubes and to subject it to an oxidative catalytic reaction in the reaction tubes;

wherein:

catalysis zones having different activities and arranged in series are provided for the catalytic reaction in the reaction tubes;

one or more catalytically active materials and one or more catalytically inactive materials are provided in the catalysis zones;

the different activity of the catalysis zones is effected by providing the one or more catalytically active materials with identical or essentially identical basic formulation, wherein the one or more catalytically active materials is or are prepared using different calcination intensities.

13. The method of claim 1, wherein a proportion of the one or more catalytically inactive materials in the respective catalysis zones to a total charge of the respective catalysis zones differs by no more than 25% relative to each other.

14. The method of claim 4, wherein the one or at least one of the multiple catalytically active materials further comprises tellurium.

15. The method of claim 14, wherein the one or more of the catalytically active materials is made at least in part from the oxides of the metals.

16. The method of claim 1, wherein the oxidative reaction is carried out at a temperature of the catalyst in a range between 280 and 450° C. and/or wherein the feed mixture is fed to the reactor at a pressure in a pressure range from 1 to 10 bar (abs.).

17. The method of claim 1, wherein the oxidative reaction is carried out at a temperature of the catalyst in a range between 300 and 400° C., and/or wherein the feed mixture is fed to the reactor at a pressure in a pressure range from 1 to 10 bar (abs.).

18. The method of claim 7, in which the oxidative reaction is carried out at a pressure in a pressure range from 2 to 6 bar (abs.).

19. The method of claim 8, wherein the water content is adjusted between 10 and 50% by volume.

20. The method of claim 8, wherein the water content is adjusted between 14 and 35% by volume.

* * * * *